(12) United States Patent
Limaye (10) Patent No.: US 10,143,797 B2
(45) Date of Patent: Dec. 4, 2018

(54) INJECTION MECHANISM UTILIZING A VIAL

(71) Applicant: Becton, Dickinson and Company, Franklin Lakes, NJ (US)

(72) Inventor: Amit Limaye, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 629 days.

(21) Appl. No.: 14/389,704

(22) PCT Filed: Apr. 8, 2013

(86) PCT No.: PCT/US2013/035661
§ 371 (c)(1),
(2) Date: Sep. 30, 2014

(87) PCT Pub. No.: WO2013/155009
PCT Pub. Date: Oct. 17, 2013

(65) Prior Publication Data
US 2015/0073384 A1    Mar. 12, 2015

Related U.S. Application Data

(60) Provisional application No. 61/686,609, filed on Apr. 9, 2012.

(51) Int. Cl.
| | |
|---|---|
| *A61M 5/145* | (2006.01) |
| *A61M 5/178* | (2006.01) |
| *A61M 5/315* | (2006.01) |
| *A61M 5/14* | (2006.01) |
| *A61M 5/165* | (2006.01) |

(Continued)

(52) U.S. Cl.
CPC ........ *A61M 5/1452* (2013.01); *A61M 5/1413* (2013.01); *A61M 5/165* (2013.01);
(Continued)

(58) Field of Classification Search
CPC ............... A61M 5/1452; A61M 5/165; A61M 5/16822; A61M 5/1413; A61M 5/31593; A61M 5/178; A61M 2205/59; A61M 2005/14513; A61M 5/204; A61M 2005/3128; A61M 5/19; A61M 5/2448; A61M 5/2053; A61M 5/2046; A61M 5/2425; A61M 2205/215; A61M 5/14526;
(Continued)

(56) References Cited

U.S. PATENT DOCUMENTS

| | | |
|---|---|---|
| 3,057,370 A | 10/1962 | Hamilton |
| 4,356,727 A | 11/1982 | Brown et al. |

(Continued)

FOREIGN PATENT DOCUMENTS

WO    WO 2010008575 A1 *    1/2010    ........ A61M 5/14216

*Primary Examiner* — Amber Stiles
(74) *Attorney, Agent, or Firm* — Dickinson Wright PLLC (57) ABSTRACT

An injection device is provided for delivering a liquid medicament. The injection device includes a housing with a first chamber for storing a supply of the medicament. The first and second chambers are coupled within the housing. The second chamber is in fluid communication with the first chamber. The injection device also includes an outlet port for dispensing the medicament outside the housing. The outlet port is coupled to the housing and in fluid communication with one of said first and second chambers.

15 Claims, 6 Drawing Sheets

(51) Int. Cl.
*A61M 5/168* (2006.01)
*A61M 5/20* (2006.01)
*A61M 5/31* (2006.01)

(52) U.S. Cl.
CPC ........ *A61M 5/16822* (2013.01); *A61M 5/178* (2013.01); *A61M 5/31593* (2013.01); *A61M 5/204* (2013.01); *A61M 2005/14513* (2013.01); *A61M 2005/3128* (2013.01); *A61M 2205/59* (2013.01)

(58) Field of Classification Search
CPC .... A61M 5/155; A61M 15/00; A61M 15/001; A61M 15/002; A61M 15/003; A61M 15/007; A61M 2005/006; A61J 1/2089
See application file for complete search history.

(56) References Cited

U.S. PATENT DOCUMENTS

| | | | |
|---|---|---|---|
| 4,717,384 A * | 1/1988 | Waldeisen | A61M 5/2053 604/143 |
| 6,090,071 A | 7/2000 | Kriesel | |
| 6,238,372 B1 * | 5/2001 | Zinger | A61J 1/2089 604/246 |
| 6,723,068 B2 | 4/2004 | Lavi et al. | |
| 7,056,307 B2 | 6/2006 | Smith et al. | |
| 7,976,505 B2 | 7/2011 | Hines et al. | |
| 2004/0035491 A1 * | 2/2004 | Castellano | A61M 5/30 141/27 |
| 2006/0280690 A1 | 12/2006 | Wright et al. | |
| 2007/0060894 A1 | 3/2007 | Dai et al. | |
| 2007/0074721 A1 * | 4/2007 | Harmer | A61M 15/0028 128/203.15 |
| 2008/0038313 A1 * | 2/2008 | Addis | A61B 17/0057 424/423 |
| 2008/0167621 A1 * | 7/2008 | Wagner | A61M 5/19 604/191 |
| 2009/0177158 A1 * | 7/2009 | Krumme | A61M 5/14526 604/143 |
| 2010/0087786 A1 * | 4/2010 | Zinger | A61J 1/2096 604/224 |
| 2010/0137833 A1 | 6/2010 | Glynn | |
| 2011/0118659 A1 | 5/2011 | Maaskamp et al. | |
| 2011/0184348 A1 | 7/2011 | Bates et al. | |

* cited by examiner

INJECTION MECHANISM UTILIZING A VIAL

CROSS-REFERENCE TO RELATED APPLICATIONS

This application claims priority under 35 USC § 119(e) from U.S. Provisional Patent Application Ser. No. 61/686,609, filed on Apr. 9, 2012, the disclosure of which is incorporated herein by reference in its entirety.

FIELD OF THE INVENTION

The present invention relates to an injection mechanism for delivering a medicament. More particularly, the present invention relates to a vial injector, including both a vial and dosing mechanism, which allows a user to inject liquid medicament from a vial without having to access the vial directly for the duration of its anticipated use.

BACKGROUND OF THE INVENTION

In certain circumstances, it is desirable to inject medicament directly into human tissue. In the contemporary art, a user draws liquid medicament from a vial using a syringe needle and then injects the medicament into a tissue layer using the same syringe needle. The contemporary art requires that the user have access to a vial and a separate syringe each time an injection is necessary.

Accordingly, the user must carry the vial and one or more syringes on his or her person at all times. Moreover, the user must repeat the tiresome process of drawing the desired medicament dose from the vial with a syringe needle and then injecting the medicament into a tissue layer using the same syringe needle each time an injection is required.

Alternatively, a user may attach a pen needle to a pen injection device to enable injection. This may be viewed as a more convenient form of human tissue injection since a medicament and dose metering are integrated into the pen. Pen injection devices generally have the added convenience of space and ease of usage and transportation, and pen needles are widely available in standard and interchangeable designs.

Pen injection devices, however, present a challenge of high thumb pressure when injecting viscous formulations, or while using small gauge needles. Additionally, the combination of pen needles and pen injection devices may not be suitable for intradermal injections due to the backpressure that the fluid needs to exceed for injection to occur.

Typically, self-injectors inject liquid medicaments into tissue areas, such as the intramuscular tissue layer, the subcutaneous tissue layer, or the intradermal tissue layer. Each of these tissue layers has specific characteristics that affect the amount of fluid pressure needed to inject a fluid into the targeted tissue layer. When injecting fluids into each of these tissue layers, the user must exert enough force on the injection device to overcome different amounts of backpressure associated with the particular tissue layer. In general, practitioners and self-injectors, such as diabetics, are familiar with the force necessary to inject fluids into the subcutaneous layer. Injections into the subcutaneous and intramuscular tissue layers can cause discomfort to the patient or self-injector because of the characteristics of the tissue, needle length and needle diameter or gauge. It is desirable to employ shorter, smaller gauge needles to achieve delivery into the intradermal tissue layer.

It is noted that when the needle lengths are shortened and needle diameters are made smaller, the fluid dynamics of the injection device changes. Additionally, the fluid dynamics between the injection device and the targeted tissue layer also change because the shorter needle length injects the fluid into a different tissue layer, such as the intradermal layer. Because the tissue density between the intramuscular, subcutaneous, and intradermal tissue layers varies, the ease with which fluid may be injected into each type of tissue layer also varies. The variation in tissue density causes changes in the backpressure exerted by the tissue against the fluid when it is injected. For instance, the backpressure associated with the intradermal tissue layer is greater than the backpressure associated with the subcutaneous tissue layer, thereby requiring a higher pressure and/or a greater force to accomplish the injection.

Currently, several pen injection systems are commercially available for subcutaneous substance delivery of medication. These pen injection systems typically use 29 to 31 gauge needles having lengths of between 5 mm and 12.7 mm, and are used to deliver the contents of a medicament cartridge, such as insulin, to the subcutaneous tissue layers of a patient rapidly and conveniently. The medicament cartridges are generally of a standard volume and size (including a fixed cross sectional area). The pressure of delivery is the quotient of the actuation force exerted by a user and the cross sectional area of the cartridge. Because the cross-sectional area of the cartridge is fixed, higher delivery pressures require higher actuation forces by the user.

A "microneedle" pen system has been developed to facilitate subcutaneous substance delivery. Such "microneedle" drug delivery systems may include shorter needles, typically less than or equal to 3 mm, with smaller diameters, in the range of 30 to 34 gauge or thinner. Such needle length and gauge size combinations are desirable to provide for sharp, yet short, point geometries that can more accurately target substance delivery to only certain selected tissue, such as the deep intradermal or shallow subcutaneous tissue layers, thereby permitting controlled fluid delivery. Current typical pen injection systems used for subcutaneous delivery are not believed optimal for use by the general population of self-injectors for delivery into the intradermal layer because of, among other things, the high backpressures associated with injecting fluid into the intradermal layers of the skin using microneedles.

Additional details of intradermal drug delivery and microneedles have been previously described in U.S. Pat. No. 6,494,865, issued on Dec. 17, 2002, U.S. Pat. No. 6,569,143, issued on May 27, 2003, U.S. Patent Application Publication No. 2007/0185460, published Aug. 9, 2007, and U.S. Patent Application Publication No. 2005/0065472, published on Mar. 24, 2005, all of which are assigned to Becton, Dickinson and Company, and the entire content of each such patent and application being incorporated herein by reference.

The intradermal tissue layer of the skin is considerably denser than the subcutaneous tissue region. The density of the intradermal tissue layer on a particular patient is, in part, a function of his or her collagen make-up (which is affected by the patient's age) and the location of the injection site on the patient's body. This increased density of the intradermal tissue layer can create a greater backpressure resistance on the injection device than the resistance created when injecting into the subcutaneous tissue region. To overcome the increased backpressure resistance when injecting into the intradermal tissue layer with a conventional drug delivery pen, the user or patient would need to exert greater actuation force (which could be substantial) on the injector device actuator or employ some sort of powered injector device. In these applications, the injector device must be designed to withstand the greater backpressure from the intradermal injection site as well as the additional force exerted by the user or patient.

Intradermal injection of insulin and other medications provides faster uptake of the drug, thereby leading to improved therapy. Existing drug delivery devices have several limitations regarding intradermal drug delivery.

First, as noted earlier, it is inconvenient for a user to carry a vial and one or more syringes on his or her person at all times to inject medicament when required over the course of a day. Moreover, it is a tiresome process for a user to draw the desired medicament dose from the vial with a syringe needle and then inject the medicament into a tissue layer using the same syringe needle each time an injection is required.

Second, the convenience of a pen injection device is offset by the force necessary to generate sufficient pressure for an intradermal injection. The pen components can be damaged by this high force, resulting in leaking and inaccuracy at the high pressures.

There is no existing injection mechanism that takes advantage of the convenience and ease of use of a pen injection device while utilizing high pressure performance of a syringe and medicament in a vial.

Therefore, a need exists to provide an injection device that enables pen-like functionality, wherein the vial and the dosing mechanism are part of one unit and the injection is provided by a replaceable pen needle. There also exists a need for an injection device that can create high pressures for injecting viscous formulations, for injections using small gauge needles, and/or for transdermal injections.

Further, there exists a need for an injection device for patient populations for which pen devices are not available or prevalent due to cost or lack of access.

SUMMARY OF THE INVENTION

An aspect of embodiments of the present invention is to substantially address the above and other concerns, and provide an injection mechanism for delivering a medicament that is simple to manufacture, by using fewer components and materials.

The above and/or other aspects and advantages are achieved by providing a delivery system for dispensing a medicament including a housing with a first chamber for storing a supply of the medicament. The first chamber and a second chamber are coupled within the housing. The second chamber is in fluid communication with the first chamber. The system also includes an outlet port for dispensing the medicament outside the housing. The outlet port is coupled to the housing and in fluid communication with one of the first and second chambers.

These and other aspects and advantages are also achieved by providing a method of dispensing a medicament with a medicament delivery system, including the steps of: coupling a first chamber to a housing, the first chamber storing the medicament, and setting a medicament dose using a second chamber, the second chamber coupled to the housing and in fluid communication with the first chamber. The dispensing steps also include transferring a fluid from one of the first and second chambers to a remaining one the first and second chambers and dispensing medicament from the remaining one of the first and second chambers to an outlet port coupled to the housing.

Additional and/or other aspects and advantages of the present invention will be set forth in the description that follows, or will be apparent from the description, or may be learned by practice of the invention

BRIEF DESCRIPTION OF THE DRAWINGS

The various objects, advantages and novel features of the exemplary embodiments of the present invention will be more readily appreciated from the following detailed description when read in conjunction with the appended drawings, in which.

DETAILED DESCRIPTION OF THE EXEMPLARY EMBODIMENTS

As will be appreciated by one skilled in the art, there are numerous ways of carrying out the examples, improvements and arrangements of vial injection devices disclosed herein. Although reference will be made to the exemplary embodiments depicted in the drawings and the following descriptions, the embodiments disclosed herein are not meant to be exhaustive of the various alternative designs and embodiments that are encompassed by the disclosed invention.

Illustrative embodiments of the present invention address the problems of prior art injection devices by providing an injection device with pen-like functionality, wherein the vial and a dosing mechanism are part of one unit and an injection is provided by a replaceable pen needle having a conventional design. Illustrative embodiments of the present invention also provide an injection device that creates high pressures for injecting medicaments by displacing a fixed volume of medicament from the vial and administering it to target tissue by using a dosing chamber that measures either air or medicament and enables the displacement of the medicament via a pen needle-like device into the target site. Although a user other than medicament recipients (for example, a health care professional) can use the illustrative embodiments, for brevity the term "user" will be employed hereinafter to refer to a patient and/or other user.

Figure 1:
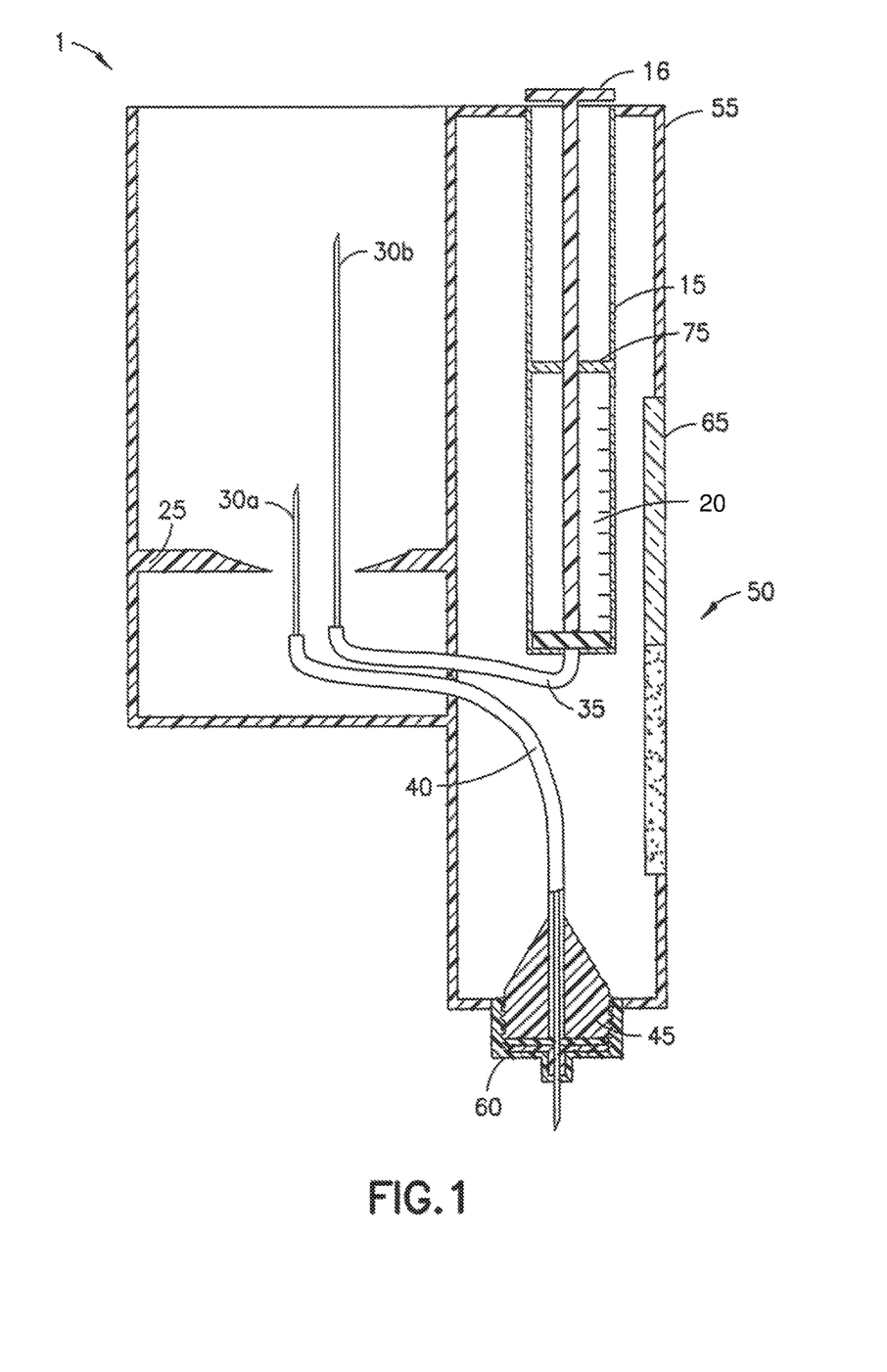
FIG. 1 is a cross-sectional view of the components of an injection mechanism capable of utilizing a vial (vial not shown) in accordance with a first embodiment of the present invention.
Figure 2A:
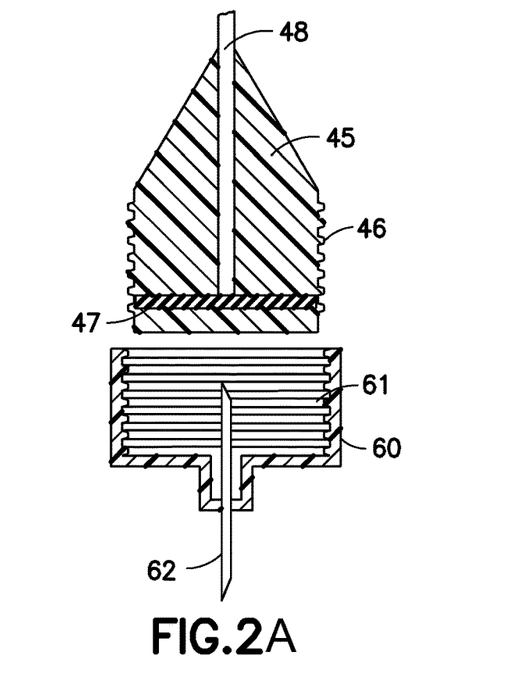
FIG. 2A is an exploded cross-sectional view of a needle assembly of the first embodiment of the injection mechanism of FIG. 1.
Figure 2B:
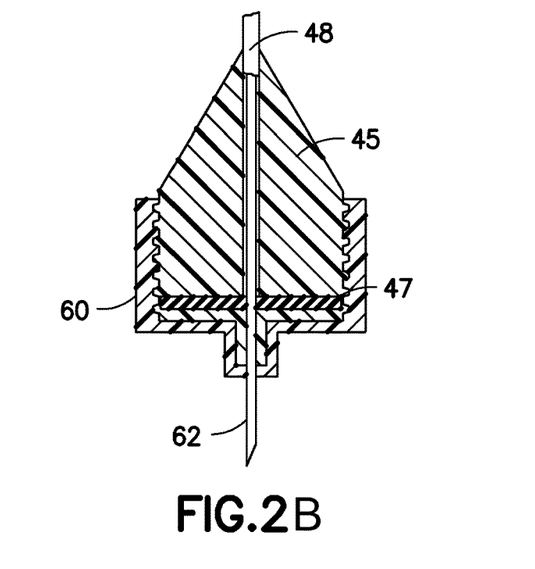
FIG. 2B is a cross-sectional view of the combined needle assembly of 2A.
Figure 3:
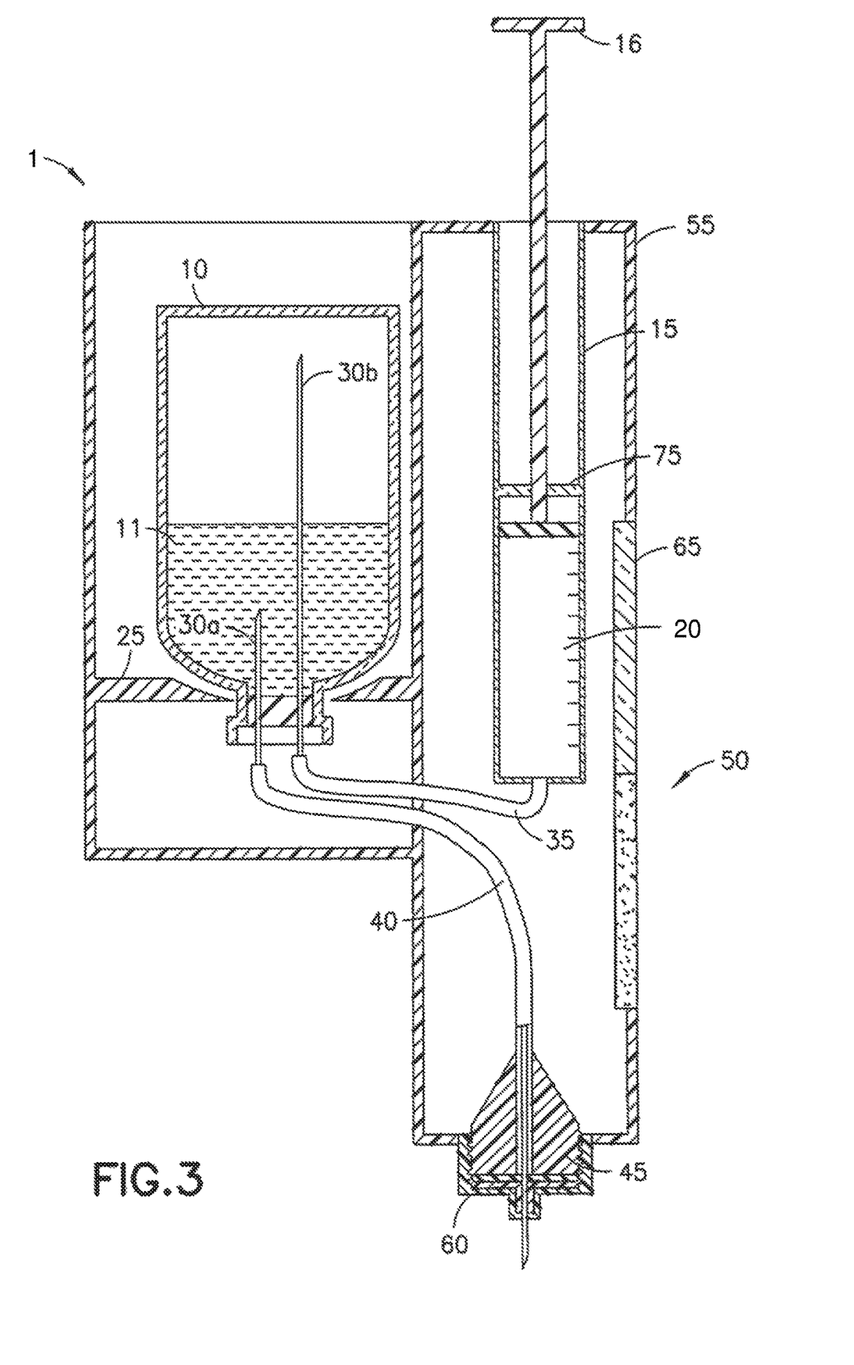
FIG. 3 is a cross-sectional view of the injection mechanism of FIG. 1 utilizing a vial.

As shown in FIGS. 1-3, an illustrative embodiment of the injection device 1 of the present invention comprises a vial 10 containing medicament 11, a dosing member 15 having a plunger and a dosing chamber 20, a retaining member 25, a hollow liquid spike 30a, a hollow air spike 30b, a dosing chamber tube 35, a fluid dispensing tube 40, a pen needle adapter 45, an orientation indicator 50, and a housing 55.

The vial 10 with liquid medicament 11 is inserted from the top of the injection device 1 and locked in place by the retaining member 25. The retaining member 25 can made of a semi-flexible material that can be flexed to receive an end portion of the vial 10 and secure the vial 10 within the housing 55. The vial 10 can be removed from the housing 55 by manually pulling on the vial until separated from the retaining member 25. Alternatively, the retaining member 25 can be manually released by actuation of a release mechanism (not shown) when the vial medicament 11 has been exhausted.

When the vial is locked into the retaining member 25, the liquid spike 30a and the air spike 30b penetrate the septum 12 of the vial. Preferably, a first end of the liquid spike 30a terminates directly above the septum 12 (within the vial 10) to maintain emersion beneath the medicament 11 until the medicament has been substantially exhausted. For illustrative purposes, however, the liquid spike 30a is shown in FIG. 3 to terminate significantly above the septum 12 (within the vial 10), to more clearly show the features of the liquid spike 30a. The air spike 30b extends significantly above the septum 12 to maintain direct fluid contact with any air in the vial 11. Spikes 30a and 30b are attached to the fluid dispensing tube 40 and dosing chamber tube 35, respectively. The dosing chamber tube 35 provides fluid connection between the dosing chamber 20 and the vial 10. The dispensing tube 40 provides fluid connection between the vial 10 and needle adapter 45 located at an outlet port of the injection device. In this embodiment, the fluid dispensing tube 40 also serves as an air vent, enabling air from the surrounding environment to enter the vial 10 when the internal pressure is reduced within the vial 10. The dispensing tube 40 can also include a filter 41 that prevents unwanted debris and/or contaminants from entering the vial 10 during venting.

FIGS. 2a and 2b respectively illustrate cross-sectional views of the needle adapter 45 and needle assembly 60 in exploded and assembled states. According to one embodiment, the needle adapter 45 includes helical threads 46 that engage and secure the needle adapter 45 to the needle assembly 60 via corresponding threads 61. As the needle assembly 60 is threaded to the needle adapter 45 a hollow needle 62 punctures the adapter septum 47, thus enabling the flow of fluid between the fluid dispensing tube 40 and the needle 62. The needle adapter 45 also includes a fluid channel 48 that is adapted to engage an end of the fluid dispensing tube 40 and provide fluid connection between the fluid dispensing tube 40 and the needle assembly 60. The needle adapter 45 and needle assembly 60 can be conventional components typically used in medicament injection pens.

To dispense medicament using the first embodiment illustrated in FIGS. 1-3, a user obtains a vial 10, and inserts and locks the vial 10 into the receiving member 25 of the injection device 1. During the insertion, the spikes 30a and 30b pierce the septum 12 of the vial 10 to access the medicament within the vial 10 and connect to tubing 35, 40 inside the housing 55.

The user attaches the needle assembly 60 to the needle adapter 45, which is connected to the fluid dispensing tube 40 inside the housing 55. This creates a path for air to flow into the vial 10.

Preferably, the dosing member 15, such as a syringe, is initially empty. That is, the plunger 16 of the dosing member plunger 16 is fully bottomed out, as shown in FIG. 1.

It is preferred that the user holds the injection device 1 vertically prior to injecting into a layer of tissue to prevent unwanted air from mixing with the medicament during injection. It is also preferred that upon attaining a vertical position with the needle 62 pointing downward, a viewing window 65 becomes available for the user to view the scale markings 70 on the dosing chamber 20. This orientation indicator 50 ensures that the user is only able to view the scale markings 70 when the injection device 1 is held in a vertical position. Embodiments of the orientation indicator 50 can use an opaque liquid filled in a tube, similar to a bubble liquid-level configuration of the contemporary art, or an opaque sliding sleeve-like device to obscure different portions of the window based on orientation of the injection device 1. For example, the opaque liquid, opaque sliding sleeve or other desired orientation mechanism will obscure the view of the scale markings 70, unless the injection device is oriented substantially vertical.

The user sets a desired dose using the dosing member 15, for example, by retracting plunger 16. By ensuring proper orientation, the orientation indicator 50 also safeguards against medicament entering the dosing member 15.

Retracting the plunger 16 of the dosing member 15 causes air to be drawn into the dosing chamber 20 via the through the air spike 30b within the vial 10. By drawing air out of the vial 10, the pressure within the vial is reduced. This pressure reduction causes air to be aspirated into the vial 10 from the outside environment via the fluid dispensing tube 40.

The plunger 16 retraction is stopped when the desired volume of air has been drawn into the dosing chamber 20 or the plunger cannot be withdrawn any further due to interference with a plunger stop 75. According to one embodiment the position of the plunger stop 75 can be adjusted to allow a medical professional to limit a maximum allowable dose volume. The stop 75 ensures that a certain dose is not exceeded in instances where potent drugs are being administered. An additional volume of air may be drawn to enable a priming action by further retraction of the plunger 16 so that air in the fluid dispensing tube 40 is replaced with the medicament prior to injection. According to one embodiment, because of the compressibility of air, the scale markings 70 compensate for the volumetric difference between the air within the dosing chamber 20 and the corresponding dose of liquid medicament 11 within the vial 10.

Upon drawing the volume of air corresponding to the desired dose into the dosing chamber 20, the user penetrates the skin with needle assembly 60 and presses the plunger 16 down while holding the injection device 1 vertical. This causes air from the dosing chamber 20 to enter the vial 10 and displace the medicament through the fluid dispense tube 40, the needle 62, and into the desired tissue site. The plunger 16 of the dosing member 15 then bottoms out and completes delivery of the desired dose to the user. The user can store the injection device 1 until its next use, at which time the above dispensing steps are repeated.

Figure 4:
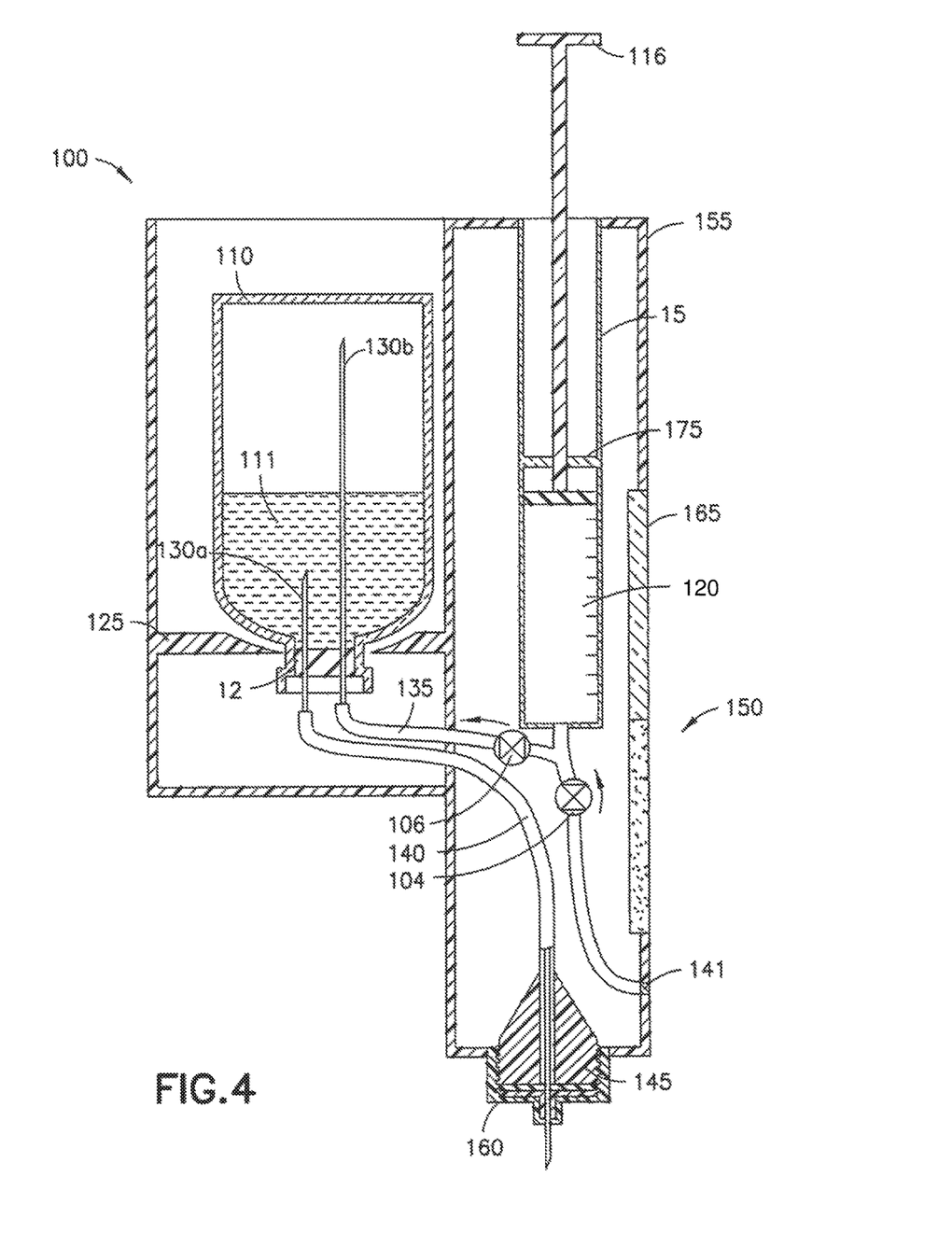
FIG. 4 is a cross-sectional view of a second embodiment of an injection mechanism utilizing a vial.

A second illustrative embodiment of the injection device of the present invention including first and second one-way valves 104 and 106, is shown in FIG. 4.

Referring to FIG. 4, a vial 110 with liquid medicament 111 is inserted from the top of the injection device 100 and locked in place by the retaining member 125. The retaining member 125 can be manually released when the vial medicament 111 has been exhausted.

When the vial 110 is locked into the retaining member 125, a hollow liquid spike 130a and a hollow air spike 130b penetrate the septum 112 of the vial 110. Although liquid spike 130a is depicted as extending substantially above the septum 112, for illustrative purposes, the liquid spike 130a preferably terminates immediately above septum 112 (within the vial 110). Spikes 130a and 130b are respectfully attached to the fluid dispensing tube 140 and dosing chamber tube 135. As shown in FIG. 4, the dosing chamber tube 135 provides fluid connection between the dosing chamber 120 and the environment outside the housing 155. The dosing chamber tube 135 also provides fluid connection between the dosing chamber 120 and the vial 110. The dispensing tube 140 provides fluid connection between the vial 110 and a needle adapter 145 located at an outlet port of the injection device 100.

In this embodiment, a first one-way valve 104 is attached to the dosing chamber tube 135 and facilitates a one-way flow of air to be aspirated into the dosing chamber 120 from the outside environment, while preventing medicament 111 from leaking out of the injection device 100. A second one-way valve 106 is attached to the dosing chamber tube 135 and facilitates one-way flow of air from the dosing chamber 120 to the vial 110 while ensuring that no medicament 111 enters the dosing chamber 120. Thus the first and second one-way valves 104 and 106 ensure that during injection, the air is transported to the vial 110. The dosing chamber tube 135 can also include a filter 141 that can prevent unwanted debris and/or contaminants from entering dosing chamber 120 or the dosing chamber tube 135.

To dispense medicament using the injection device 100 illustrated in FIG. 4, a user attaches a hollow-needle pen needle assembly 160 to the needle adapter 145, which is connected to the fluid dispense tube 140 inside the housing 155.

Preferably the dosing member 115, such as a syringe, is initially empty. That is, the plunger 116 of the dosing member 116 is fully bottomed out. Similar to the first illustrative embodiment of the present invention, the user holds the injection device 100 vertically prior to inserting the needle assembly 160 into a layer of tissue. Upon attaining a vertical position with the needle assembly 160 pointing downward, a viewing window 165 of an orientation indicator 165 becomes available for the user to view the scale marking 170 on the dosing chamber 120.

The user sets a desired dose using the dosing member 115 by retracting the plunger 116. As the plunger 116 is retracted, the first one-way valve 104 attached to dosing chamber tube 135 allows air to be aspirated into the dosing chamber 120.

The plunger 116 retraction can be stopped when the desired volume of air has been drawn into the dosing chamber 120 or the plunger is blocked by the plunger stop 175. An additional volume of air may be drawn by further retracting the plunger 116 to enable a priming action whereby air in the fluid dispensing tube 140 is replaced with the medicament 111 prior to injection. The user penetrates the skin by inserting the needle assembly 160 into the desired tissue and then pressing the plunger 116 down while holding the injection device 100 in the vertical orientation. The second one-way valve 106 ensures that air from the dosing chamber 120 enters the vial 110 and displaces the medicament 111 through the fluid dispensing tube 140, the needle assembly 160, and into the desired tissue site.

As the plunger 116 of the dosing member 115 bottoms out the delivery of the desired dose of medicament 111 is completed. The user can store the injection device 100 until its next use, at which time the above dispensing steps are repeated.

Figure 5:
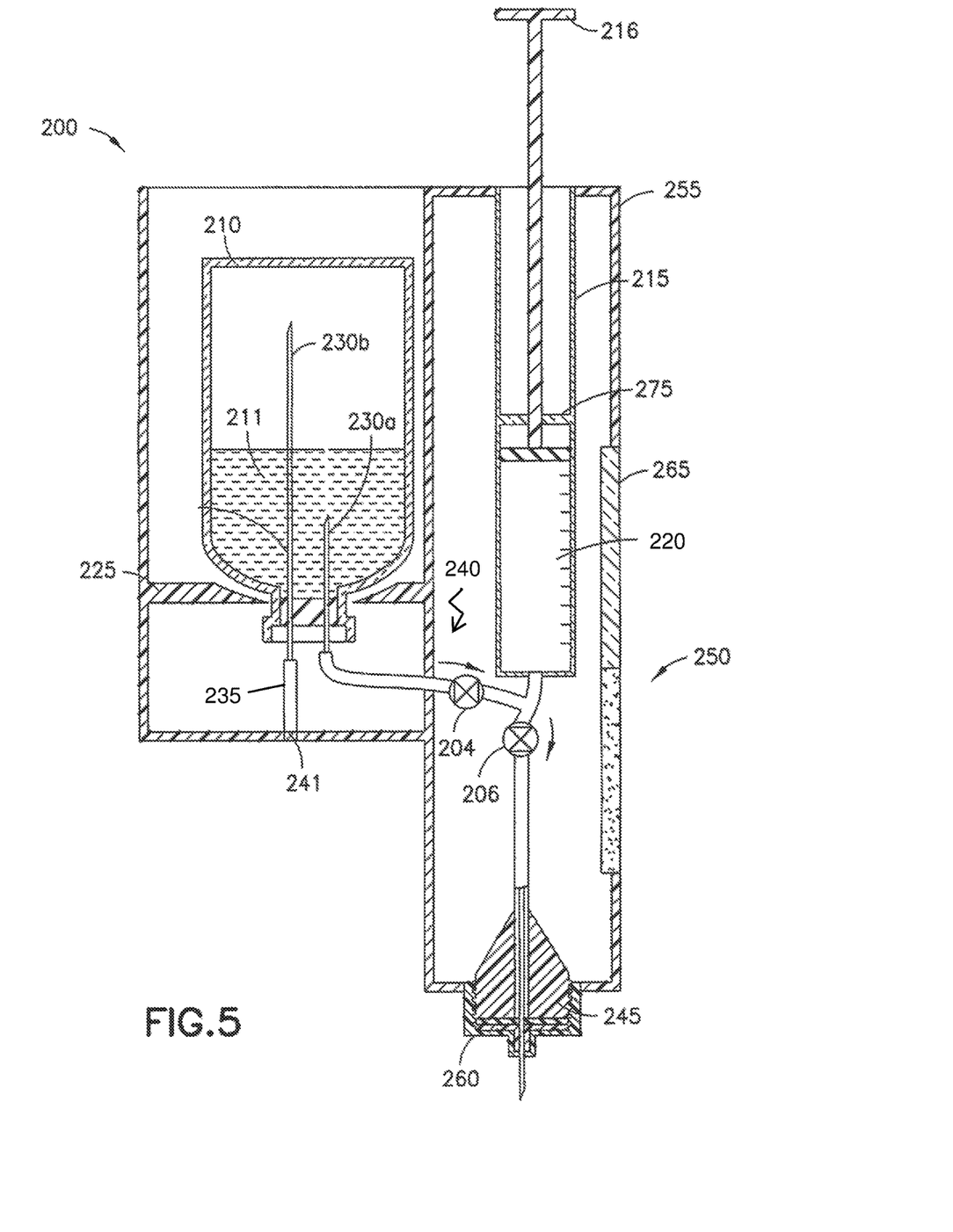
FIG. 5 is a cross-sectional view of a third embodiment of an injection mechanism utilizing a vial.

A third illustrative embodiment of the present invention is shown in FIG. 5. This embodiment differs from the first two embodiments in that medicament enters the dosing chamber 220, whereas in the first two embodiments only air enters the respective dosing chamber 215.

Referring to FIG. 5, a vial 210 with liquid medicament 211 is inserted from the top of the injection device 200 and locked in place by the retaining member 225. The retaining member 225 can be manually released when the vial medicament 211 has been exhausted.

When the vial 210 is locked into the retaining member 225, a hollow liquid spike 230a and a hollow air spike 230b penetrate a septum 212 of the vial 210. Spikes 230a and 230b, respectively, are attached to a fluid dispensing tube 240 and a venting tube 235. Although liquid spike 230a is depicted as extending substantially above the septum 212, for illustrative purposes, the liquid spike 230a preferably terminates immediately above septum 212 (within the vial 110). The venting tube 235 provides fluid connection between the vial 210 and the environment outside the housing 255. The dispensing tube 240 provides fluid connection between the vial 210 and the dosing chamber 220 and between the dosing chamber 220 and a needle adapter 245 located at an outlet port of the injection device 200.

In this embodiment, a first one-way valve 204 is attached to the dispensing tube 240 and facilitates a one-way flow of medicament into the dosing chamber 220. A second one-way valve 206 is attached to the dispensing tube 240 and facilitates one-way flow of medicament from the dosing chamber 220 to the needle assembly attached to the needle adapter 245. Thus, the first and second one-way valves 204 and 206 ensure that the medicament is transported from the vial 210, to the dosing chamber 220 and then to the needle assembly 260. The venting tube 235 can also include a filter 241 and a one-way valve (not shown) that can prevent unwanted debris and/or contaminants from entering the vial 110 during venting of the vial 210.

To dispense medicament using the injection device 200 illustrated in FIG. 5, the user attaches a hollow-needle pen needle assembly 260 to the needle adapter 245, which is connected to the fluid dispensing tube 240 inside the housing 255.

Preferably, the dosing member 215, such as a syringe, is initially empty with a plunger 216 of the dosing member 215 fully bottomed out. The user holds the injection device 200 vertically prior to injecting into a layer of tissue. Upon attaining a vertical position with the needle assembly pointing downward, the user can view a viewing window 265 to see the scale markings 270 on the dosing chamber 220.

The user the sets a desired dose using the dosing member 215 by retracting the plunger 216. The first one-way valve 104 attached to dispensing tube 240 causes only medicament to be drawn into the dosing chamber 220 from the vial 210 while the second one-way valve 206 ensures that no air enters the dosing chamber 220 from the needle assembly 260.

The retraction of plunger 216 can be stopped when the desired volume of medicament has been drawn into the dosing chamber 220 or when the plunger 216 abuts the plunger stop 275. But, an additional volume of medicament may be drawn by further retracting the plunger 216 to enable a priming action. The user penetrates the skin and administers the dose by depressing the plunger 216.

Because of the plunger displacement, medicament from the dosing chamber 220 of the dosing member 215 is expelled from the injection device 200 through the fluid dispensing tube 240, the needle assembly 260, and into the desired tissue site. The first one-way valve 204 ensures that the medicament does not reenter the vial 210.

As the plunger 216 of the dosing member 215 bottoms out, the delivery of the desired dose of medicament 211 is completed. The user can store the injection device 200 until its next use, at which time the above dispensing steps are repeated. Although an orientation indicator can be used in conjunction with this embodiment similar to those of the previous embodiments, an advantage of this embodiment of the present invention is that the injection device 200 does not have any restrictions on orientation while injecting medicament into the desired tissue site.

Figure 6:
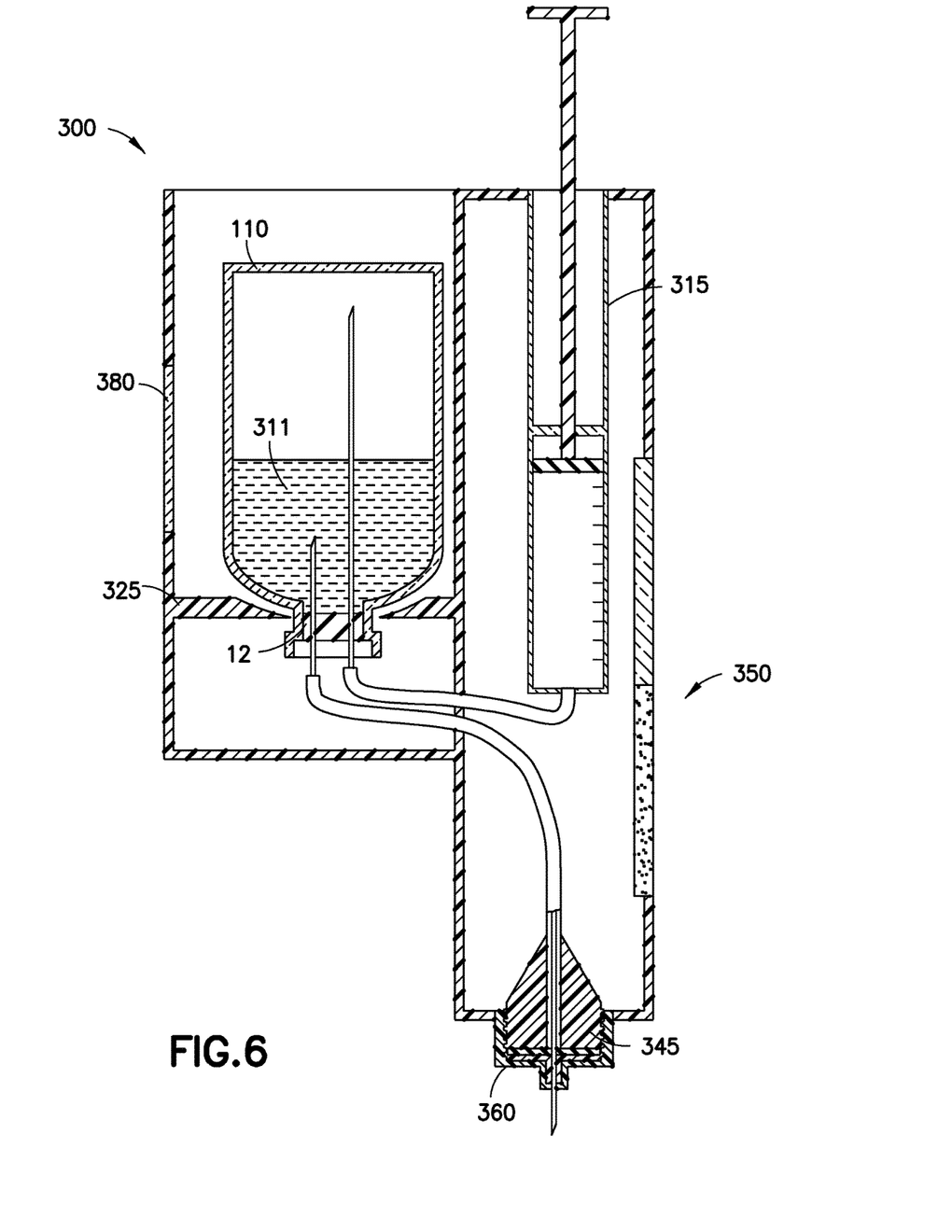
FIG. 6 is a cross-sectional view of a fourth embodiment of an injection mechanism utilizing a vial.

A fourth illustrative embodiment of the present invention is shown in FIG. 6. This embodiment is similar to the embodiment of FIGS. 1-3, except that a viewing window 380 may be provided to enable viewing of liquid medicament 311 level in a vial 310. Alternatively, the viewing window 380 may be used to confirm that the medicament and the injection device 300 are correctly matched using, for example, matching bar codes or RF-ID tags. For example, the concentration of medicament within a vial must match the calibrated dosage markings on an injection device to ensure proper dosage. The viewing window 380 and other features of the fourth embodiment are shown in FIG. 6 as added features combined with the first embodiment described above. But, each of the features described herein with respect to the fourth embodiment can be similarly combined with each of the above-discussed embodiments.

Additionally, a vial receiving member 325 of the injection device 300 can be modified to be specific to a certain vial shape or size, to ensure that an incorrect vial 310 cannot be used with injection device 300.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined by the appended claims and their equivalents.

The invention claimed is:

1. A delivery system for dispensing a medicament comprising:
   a housing;
   a first chamber for storing a supply of the medicament, the first chamber being coupled within the housing;
   a second chamber coupled within the housing;
   a dosing tube providing fluid communication between the first and second chambers;
   an outlet port for dispensing the medicament outside the housing, the outlet port being coupled to the housing; and
   a dispensing tube providing fluid communication between the first chamber and the outlet port; and
   a needle removably coupled to the outlet port to facilitate injection into a user;
   wherein the dosing tube communicates air from the second chamber to the first chamber, causing displacement of the medicament from the first chamber to the outlet port via the dispensing tube.

2. The delivery system of claim 1, wherein the first chamber comprises a vial.

3. The delivery system of claim 1, wherein the second chamber comprises a syringe.

4. The delivery system of claim 1, wherein the first chamber is removable.

5. A delivery system for dispensing a medicament comprising:
   a housing;
   a first chamber for storing a supply of the medicament, the first chamber being coupled within the housing;
   a second chamber coupled within the housing;
   a dosing tube providing fluid communication between the first and second chambers;
   an outlet port for dispensing the medicament outside the housing, the outlet port being coupled to the housing; and
   a dispensing tube providing fluid communication between the first chamber and the outlet port; and
   a one-way valve attached to the dosing tube permitting fluid flow only from the second chamber to the first chamber;
   wherein the dosing tube communicates air from the second chamber to the first chamber, causing displacement of the medicament from the first chamber to the outlet port via the dispensing tube.

6. The delivery system of claim 5, wherein the dosing tube also connects the second chamber to an environment exterior to the housing, providing fluid communication between the exterior environment and the second chamber.

7. The delivery system of claim 6, further comprising:
   a filter fixed within the dosing tube between the environment and the second chamber.

8. A delivery system for dispensing a medicament comprising:
   a housing;
   a first chamber for storing a supply of the medicament, the first chamber being coupled within the housing;
   a second chamber coupled within the housing;
   a dosing tube providing fluid communication between the first and second chambers;
   an outlet port for dispensing the medicament outside the housing, the outlet port being coupled to the housing;
   a dispensing tube providing fluid communication between the first chamber and the outlet port; and
   a one-way valve attached to the dosing tube permitting fluid flow only from the second chamber to the first chamber;
   wherein the dosing tube communicates air from the second chamber to the first chamber, thereby forcing the medicament from the first chamber to the outlet port via the dispensing tube;
   wherein the dosing tube also connects the second chamber to an environment exterior to the housing, providing fluid communication between the exterior environment and the second chamber; and
   wherein the delivery system further comprises a second one-way valve attached to the dosing tube permitting fluid flow only from the environment to the second chamber.

9. A delivery system for dispensing a medicament comprising:
   a housing;
   a first chamber for storing a supply of the medicament, the first chamber being coupled within the housing;
   a second chamber coupled within the housing, the second chamber being in fluid communication with the first chamber;
   an outlet port for dispensing the medicament outside the housing, the outlet port being coupled to the housing and in fluid communication with one of said first and second chambers; and an orientation indicator for identifying to a user when the delivery system is positioned in a substantially vertical orientation, wherein the orientation indicator comprises a viewing window that becomes available for the user to view the second chamber upon attaining the substantially vertical orientation.

10. A method of dispensing a medicament with a medicament delivery system, comprising the steps of:
coupling a first chamber to a housing, the first chamber storing the medicament;
setting a medicament dose using a second chamber, the second chamber being coupled to the housing and in fluid communication with the first chamber; and
transferring a fluid from the second chamber to the first chamber, causing the medicament to be expelled from the first chamber to an outlet port coupled to the housing.

11. The method of claim 10, wherein the fluid is not the medicament.

12. The method of claim 10, further comprising a step of:
transferring the fluid from an environment outside the housing into the second chamber before the transferring of the fluid from the second chamber to the first chamber.

13. A method of dispensing a medicament with a medicament delivery system, comprising the steps of:
coupling a first chamber to a housing, the first chamber storing the medicament;
setting a medicament dose using a second chamber, the second chamber being coupled to the housing and in fluid communication with the first chamber;
transferring a fluid from the second chamber to the first chamber, thereby forcing the medicament from the first chamber to an outlet port coupled to the housing; and
transferring the fluid from an environment outside the housing into the second chamber via the first chamber.

14. A delivery system for dispensing a medicament comprising:
a housing;
a first chamber for storing a supply of the medicament, the first chamber being coupled within the housing;
a second chamber coupled within the housing;
a dosing tube providing fluid communication between the first and second chambers;
an outlet port for dispensing the medicament outside the housing, the outlet port being coupled to the housing; and
a dispensing tube providing fluid communication between the first chamber and the outlet port;
wherein the dosing tube communicates air from the second chamber to the first chamber, thereby forcing the medicament from the first chamber to the outlet port via the dispensing tube; and
wherein the air is transferred from an environment outside the housing into the second chamber via the first chamber.

15. A delivery system for dispensing a medicament comprising:
a housing;
a first chamber for storing a supply of the medicament, the first chamber being coupled within the housing;
a second chamber coupled within the housing;
a dosing tube providing fluid communication between the first and second chambers;
an outlet port for dispensing the medicament outside the housing, the outlet port being coupled to the housing;
a dispensing tube providing fluid communication between the first chamber and the outlet port;
an air spike connected to the dosing tube and terminating in an air space of the first chamber when the delivery system is positioned in a substantially vertical orientation; and
a fluid spike connected with the dispensing tube and terminating within remaining medicament of the first chamber when the delivery system is positioned in the substantially vertical orientation;
wherein the dosing tube communicates air from the second chamber to the first chamber, thereby forcing the medicament from the first chamber to the outlet port via the dispensing tube.

* * * * *